(12) United States Patent
Smith et al.

(10) Patent No.: US 7,037,277 B1
(45) Date of Patent: May 2, 2006

(54) SYSTEM AND METHOD FOR FLUID MANAGEMENT IN A CONTINUOUS FLUID COLLECTION AND SENSOR DEVICE

(75) Inventors: Alan Smith, Atlanta, GA (US); Harry K. Delcher, Duluth, GA (US); Jonathan A. Eppstein, Atlanta, GA (US); David Farquhar, Commerce, GA (US); Michael R. Hatch, Sugar Hill, GA (US); Krishna Kumar, Duluth, GA (US)

(73) Assignees: SpectRx, Inc., Norcross, GA (US); Altea Technologies, Inc., Tucker, GA (US)

( * ) Notice: Subject to any disclaimer, the term of this patent is extended or adjusted under 35 U.S.C. 154(b) by 0 days.

(21) Appl. No.: 09/357,452

(22) Filed: Jul. 20, 1999

Related U.S. Application Data

(60) Provisional application No. 60/139,970, filed on Jun. 18, 1999, provisional application No. 60/138,739, filed on Jun. 11, 1999, and provisional application No. 60/093,534, filed on Jul. 21, 1998.

(51) Int. Cl.
*A61B 10/00* (2006.01)

(52) U.S. Cl. ....................... 600/584; 600/309
(58) Field of Classification Search ......... 600/309–323, 600/573, 576, 583, 584
See application file for complete search history.

(56) References Cited

U.S. PATENT DOCUMENTS

| | | |
|---|---|---|
| 3,847,138 A | 11/1974 | Gollub |
| 4,006,743 A | 2/1977 | Kowarski |
| 4,151,845 A | 5/1979 | Clemens |

(Continued)

FOREIGN PATENT DOCUMENTS

| | | |
|---|---|---|
| EP | 0 596 615 A1 | 5/1994 |
| EP | 0 812 570 A1 | 12/1997 |
| GB | 1498332 | 1/1979 |
| WO | WO 94/06019 | 3/1994 |
| WO | WO 94/09713 | 5/1994 |
| WO | WO 94/14062 | 6/1994 |
| WO | WO 96/00110 | 1/1996 |
| WO | WO 97/04832 | 2/1997 |

(Continued)

OTHER PUBLICATIONS

"Ultraviolet–Laser Ablation of Skin" Lane et al. 121 Arch. Dermatol., 609–617 (1985).
"Controlled Removal of Human Stratum Corneum by Pulsed Laser" Jacques et al., 88 J. Invest. Dermatol., 88–93 (1987).

*Primary Examiner*—Eric F. Winakur
(74) *Attorney, Agent, or Firm*—Altera Law Group, LLC

(57) ABSTRACT

A fluid collection and sensor device for placement over at least one artificial opening made in a biological membrane for measuring a characteristic of a biological fluid collected from the tissue through the at least one artificial opening. The device comprises a sensor positioned in a flow path of the biological fluid for contacting a quantity of the biological fluid and generating an indication of a characteristic of the biological fluid. According to one aspect of the invention, a waste fluid storage element, such as a reservoir, is positioned in the device to collect the biological fluid after it has made contact with the sensor. According to another aspect of the invention, various surfaces of the fluid flow path of the fluid collection and sensor device are treated with an agent to limit or minimize clotting, aggregation or sepsis of the biological fluid, blockage or clogging of the flow path or degradation of the sensor. According to still another aspect of the invention, various configurations of a fluid sensor and collection device are provided that are designed to ensure that measurements are made on independent fluid samples.

44 Claims, 10 Drawing Sheets

U.S. PATENT DOCUMENTS

| | | |
|---|---|---|
| 4,409,966 A | 10/1983 | Lambrecht |
| 4,832,034 A | 5/1989 | Pizziconi et al. |
| 5,339,830 A | 8/1994 | Blake, III |
| 5,458,140 A | 10/1995 | Eppstein et al. |
| 5,582,184 A | 12/1996 | Erickson et al. |
| 5,640,954 A | 6/1997 | Pfeiffer et al. |
| 5,682,233 A | 10/1997 | Brinda |
| 5,697,899 A | 12/1997 | Hillman et al. |
| 5,746,217 A | 5/1998 | Erickson et al. |
| 5,820,570 A | 10/1998 | Erickson et al. |
| 5,885,211 A | 3/1999 | Eppstein et al. |
| 6,071,249 A | 6/2000 | Cunningham et al. |

FOREIGN PATENT DOCUMENTS

| | | |
|---|---|---|
| WO | WO 97/12242 | 4/1997 |
| WO | WO 97/38126 | 10/1997 |
| WO | WO 97/42882 | 11/1997 |
| WO | WO 97/42883 | 11/1997 |
| WO | WO 97/42885 | 11/1997 |
| WO | WO 97/42886 | 11/1997 |
| WO | WO 97/42888 | 11/1997 |
| WO | WO 97/43962 | 11/1997 |
| WO | WO 98/00193 | 1/1998 |

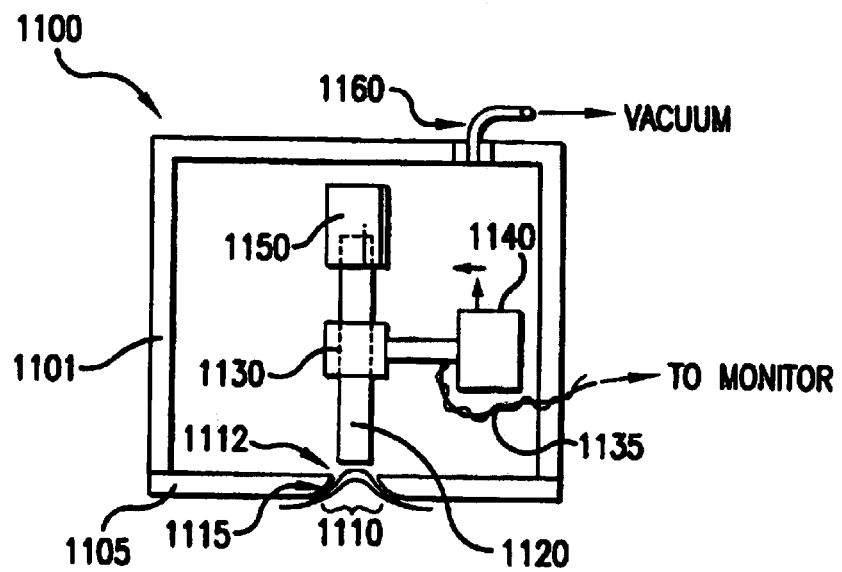
FIG.14
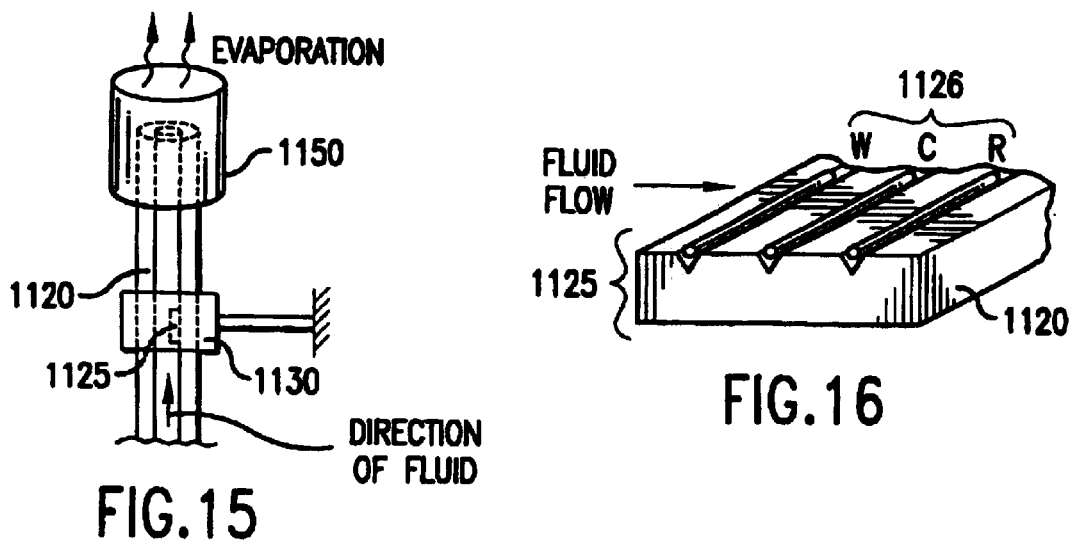
FIG.15
FIG.16

SYSTEM AND METHOD FOR FLUID MANAGEMENT IN A CONTINUOUS FLUID COLLECTION AND SENSOR DEVICE

This application claims priority to U.S. Provisional Application No. 60/093,534 filed Jul. 21, 1998; U.S. Provisional Application No. 60/138,739 filed Jun. 11, 1999; and U.S. Provisional Application No. 60/139,970 filed Jun. 18, 1999.

BACKGROUND OF THE INVENTION

The present invention is directed to a continuous fluid collection and monitoring system, and more particularly to a system and method for handling fluid in a continuous fluid collection device.

Prior art single use glucose devices do not address the need to remove fluid from the sensor before measurement of a new fluid sample because these devices are used only on one fluid sample.

In a continuous fluid collection and monitoring system, biological fluid is collected on a continuous basis in a tissue interface device positioned on or about the tissue and caused to flow across a sensor therein. It may be desirable to remove the fluid from the sensor after it has already contacted the sensor and generated a reading, so that new fluid samples can be made to contact the sensor in order to obtain new readings based only on the properties of the new fluid samples. This is particularly important when the fluid samples that are sensed are at a low fluid flow rate, such as microliters per hour, where it is desirable to obtain readings as efficiently as possible. In addition, the fluid flow through the device must be maintained to ensure accurate sensor measurements.

SUMMARY OF THE INVENTION

Briefly, one aspect of the present invention is directed to a fluid collection and sensor device for placement over at least one artificial opening made in a biological membrane for measuring a characteristic of a biological fluid collected from the tissue through at least one artificial opening. The device comprises a sensor positioned in a flow path of the biological fluid for contacting a quantity of the biological fluid and generating an indication of a characteristic of the biological fluid, such as a level of a selected analyte; and a reservoir positioned in the device to collect the biological fluid after it has made contact with the sensor. In one embodiment, the reservoir is movable into and out of contact with the sensor to remove fluid therefrom. In another embodiment, a quantity of purge media is stored in the device for controlled release to flush the sensor clean of fluid prior to a measurement on a new fluid sample.

Another aspect of the invention is to treat various components of the fluid flow path in a fluid collection and sensor device with agent to limit or minimize clotting, aggregation, agglutination or sepsis of the biological fluid, blockage or clogging of the flow path or degradation of the sensor. The various treatments are achieved by surface coating, surface modification by various means (corona discharge, gas plasma, etc.) entrainment within the components of the device, such as a semi-porous polymer for controlled release.

According to another aspect of the invention, various configurations of a fluid sensor and collection device are provided that are designed to ensure that measurements are made on independent fluid samples.

The above and other objects of the present invention will become more readily apparent when reference is made to the following description taken in conjunction with the accompanying drawings.

BRIEF DESCRIPTION OF THE DRAWINGS

FIG. 14 is a diagram showing a fluid collection and sensor device featuring a micro-capillary tube that is useful in controlling introduction of new fluid onto a sensor.

FIG. 15 is a detailed diagram of the micro-capillary tube forming a part of the device shown in FIG. 14.

FIG. 16 is a partial sectional view of a portion of the micro-capillary tube showing the sensor electrodes incorporated in the wall of the micro-capillary tube.

DETAILED DESCRIPTION OF THE INVENTION

Definitions

As used herein, the term "tissue" means an aggregate of cells of a particular kind, together with their intercellular substance, that forms a structural material. At least one surface of the tissue is preferably, but not necessarily, accessible to electromagnetic radiation so that one embodiment of the invention can be carried out. The preferred tissue is the skin. Other tissues suitable for use with this invention include mucosal tissue and soft organs.

As used herein, the term "biological membrane" means the outer layer of an organism, such as skin or mucous membrane, the structure separating one area of an organism from another, such as a capillary wall, or the outer layer of an organism which separates the organism from its external environment, such as skin, buccal mucosa or other mucous membrane.

As used herein, the term "biological fluid" means blood serum, whole blood, interstitial fluid, lymph fluid, spinal fluid, plasma or any combination of these fluids. "Interstitial fluid" means the clear fluid that occupies the space between the cells in the body.

As used herein, "poration," "microporation," or any such similar term means the formation of a small hole, opening or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures. The size of the hole or "micropore" so formed is approximately 1–1000 μm in diameter. It is to be understood that the term "micropore" is used in the singular form for simplicity, but that it multiple openings or pores may be formed by the integrated device according to the present invention.

As used herein, "artificial opening" means any physical breach of the biological membrane of a suitable size for delivering a compound or extracting a fluid therethrough, including micropores.

As used herein, the term "suction" or "pressure" relates to the relative pressure as compared to the internal pressure of the organism to which the system is interfaced. "Vacuum" is used synonymously with the term "suction."

As used herein, the term "integrated device" means a device suitable for forming small holes or micropores in tissue, collecting a biological fluid from the tissue (preferably through the micropores so created) and analyzing the biological fluid to determine a characteristic thereof.

Figure 1:
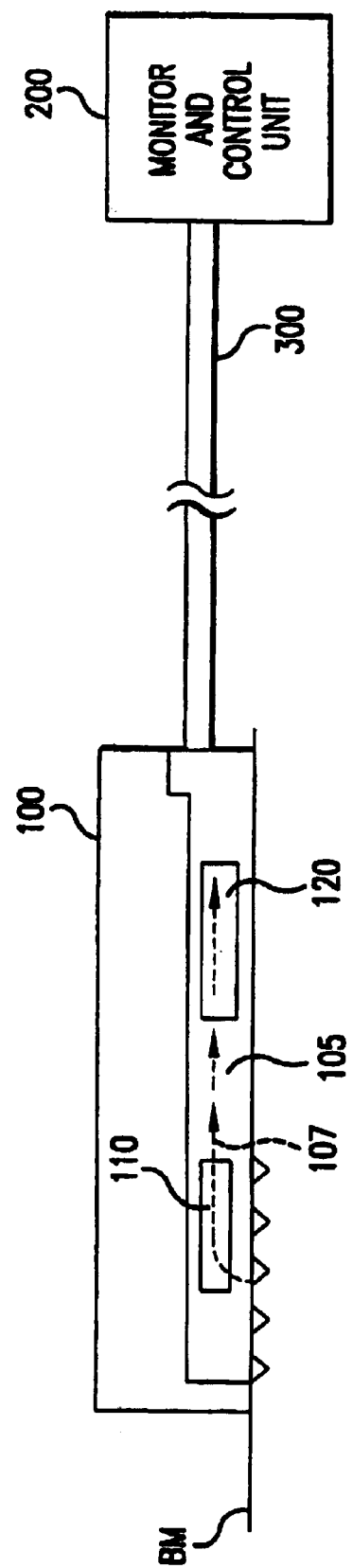
FIG. 1 is a schematic diagram showing a fluid collection and sensor device featuring a waste fluid collection element in the environment of a continuous monitoring system.

Referring first to FIG. 1, a fluid collection and sensor device is shown at reference numeral 100 as part of a continuous fluid collection and monitoring system, such as the system disclosed in commonly assigned U.S. application Ser. No. 09/357,471, entitled "System And Method For Continuous Analyte Monitoring," filed on even date. The fluid collection and sensor device 100, also called a tissue interface device, is designed to be positioned on or about the surface of a biological membrane (BM) to collect and monitor fluid that is harvested through one or more artificial openings created in the biological membrane. The fluid collection and sensor device 100 comprises a sensor 110 and a waste fluid storage element 120. These elements are contained within a flexible housing that is tissue-compatible.

The device 100 is coupled to a monitor and control unit 200 that includes a source of suction and acts as a controller for controlling the application of suction over the sensor 110 to draw biological fluid out of the tissue via one or more artificial openings in the biological membrane so that the fluid is transported and makes contact with the sensor 110. A fluid flow path 105 for the biological fluid is defined in the device 100 for drawing the fluid from the tissue to the sensor 110 and ultimately to the waste fluid storage element 120. Direction of fluid flow is shown by arrow 107. The sensor 110 may be any type of sensor, such as an analyte sensor that determines the concentration of an analyte in the biological fluid. A glucose sensor is an example. One or more electrically conductive and/or optic lead lines connect the sensor to the monitor and control unit 200. The lead lines from the sensor may be contained within a connector 300 that couples the monitor and control unit 200 to the fluid collection and sensor device 100. The connector also communicates suction or positive pressure to the fluid collection and sensor device 100. The lead lines can include one or more optical fiber elements useful to optically read the sensor 110 remotely from the monitor and control unit 200 if the sensor 110 is a type that is optically read. Alternatively, the device 100 may contain a light source, detector, suitable optics and electronics to support the use of an optically read sensor 110.

The waste fluid storage element 120 collects biological fluid after it has contacted the sensor 110. Suction applied from the monitor and control unit 200 creates a pressure differential between the organism's internal pressure and that of the system to draw the fluid into the device 100 onto the sensor 110 and ultimately deposits the fluid into the waste fluid storage element 120 so that new samples of the biological fluid are drawn in to contact the sensor 110 for new an independent readings. The organism's internal pressure is, for example, tissue pressure, intercellular or interstitial pressure, lymph fluid pressure, arterial pressure, capillary blood pressure, possibly intracellular pressure, the internal pressure of an organ (kidney, brain, spinal cord, etc.), or pressure of an abnormal tissue mass (tumor, cyst, etc.). In this manner, the fluid is collected and monitored on a continuous basis, at flow rates in the range of microliters per hour in order to obtain measurements on a periodic basis. Because small fluid volumes are continuously collected by the device 100, over a period of several hours to many days, it is practical to utilize a waste storage element 120 to store the fluid that has already been sensed by the sensor 110. The volume capacity of the waster fluid storage element 120 is variable depending on the application. A range is, for example, of 0.1 mL to 2 mL.

In a basic embodiment, the waste fluid storage element 120 may comprise one or more layers of mesh wicking material that wicks fluid away or off of the sensor 110. Preferably, the mesh layer would be designed to wick off the fluid only after it has been on the sensor 110 for a sufficient period of time to allow a measurement. This could be controlled by fabricating the mesh layer with a specified surface tension so that it can wick fluid away from the sensor no faster than a certain rate to ensure that the fluid has made contact with the sensor 110 for a sufficient period of time. Alternatively, the waste fluid storage element comprises a reservoir that includes one or more layers of wicking material therein to absorb fluid collected in the reservoir. The surface tension effects of the mesh layer are controlled by selection of materials, type of weave used, three dimensions, treatment of the mesh with surface tension modifiers such as surfactants, hydrophobic compounds, or any combinations of these techniques as is well known in the art.

Figure 2:
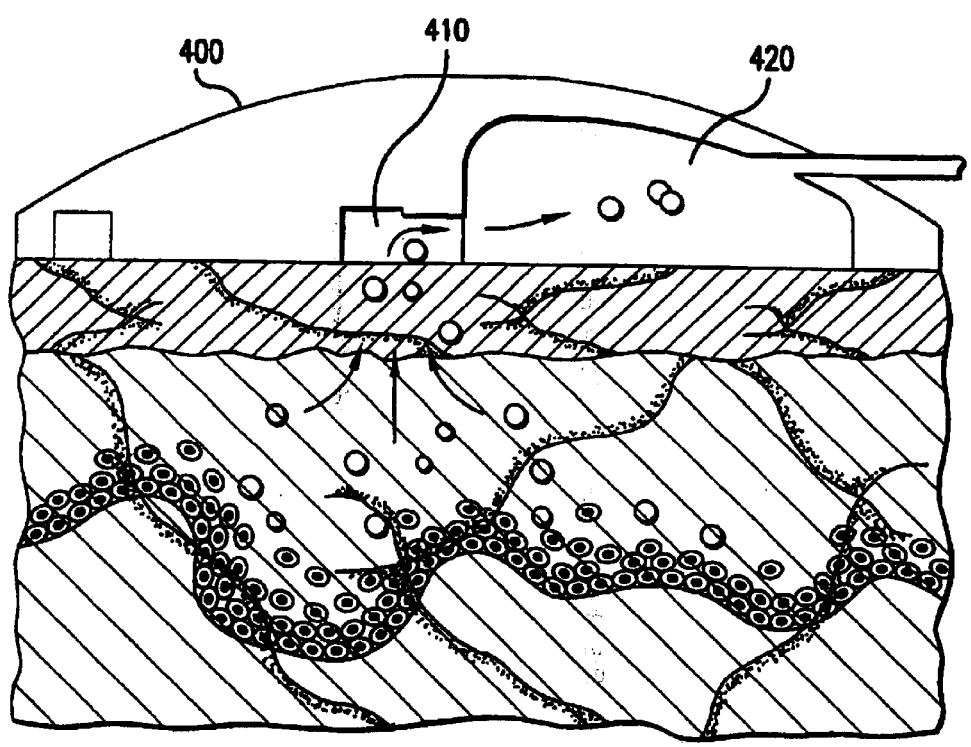
FIG. 2 is a cross-section view of one embodiment of a fluid collection and sensor device having a reservoir for storing waste fluid according to one embodiment of the invention.
Figure 3:
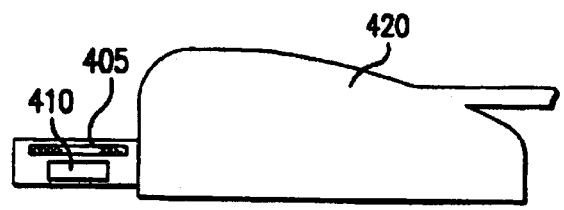
FIG. 3 is a side view of the reservoir of the device shown in FIG. 2.

FIGS. 2 and 3 illustrate an embodiment of a fluid collection and sensor device 400 comprising a waste fluid reservoir 420 positioned downstream of a sensor 410. Fluid flows out of the tissue across the sensor 410 and then into the waste fluid reservoir 420. Optionally, a mesh element 405 is placed over the sensor 410. The mesh element 405 is optionally fabricated to promote an even, bubble-free fluid flow across the sensor 410. This mesh element 405 is optionally treated with various compounds such as surface tension modifiers, such as a surfactant, to assist in controlling the fluid flow across the sensor, or agents designed to keep the sensor element free from protein aggregation, protein agglutination, fibrinogenosis, cellular attachment, bacterial growth, or sepsis, as well as to prevent the blocking or reduction of fluid flow across the sensor. The reservoir 420 is preferably made from a suitable absorptive media such as a bonded fiber material that is commonly used in liquid transfer wicks or filters. For example, these materials may be made by bonding cellulose acetate, polyester, nylon or polyolefin fibers. The fibers are optionally oriented to promote movement of the biological fluid in the flow path across the sensor 410 and into the reservoir 420. An example of a suitable reservoir is a media sold by Filtrona Richmond, Inc. under the trademark Transorb™, which is commonly used as downstream absorptive media in flow-through diagnostic devices and in other applications requiring absorption and retention of excess liquid.

Figure 4:
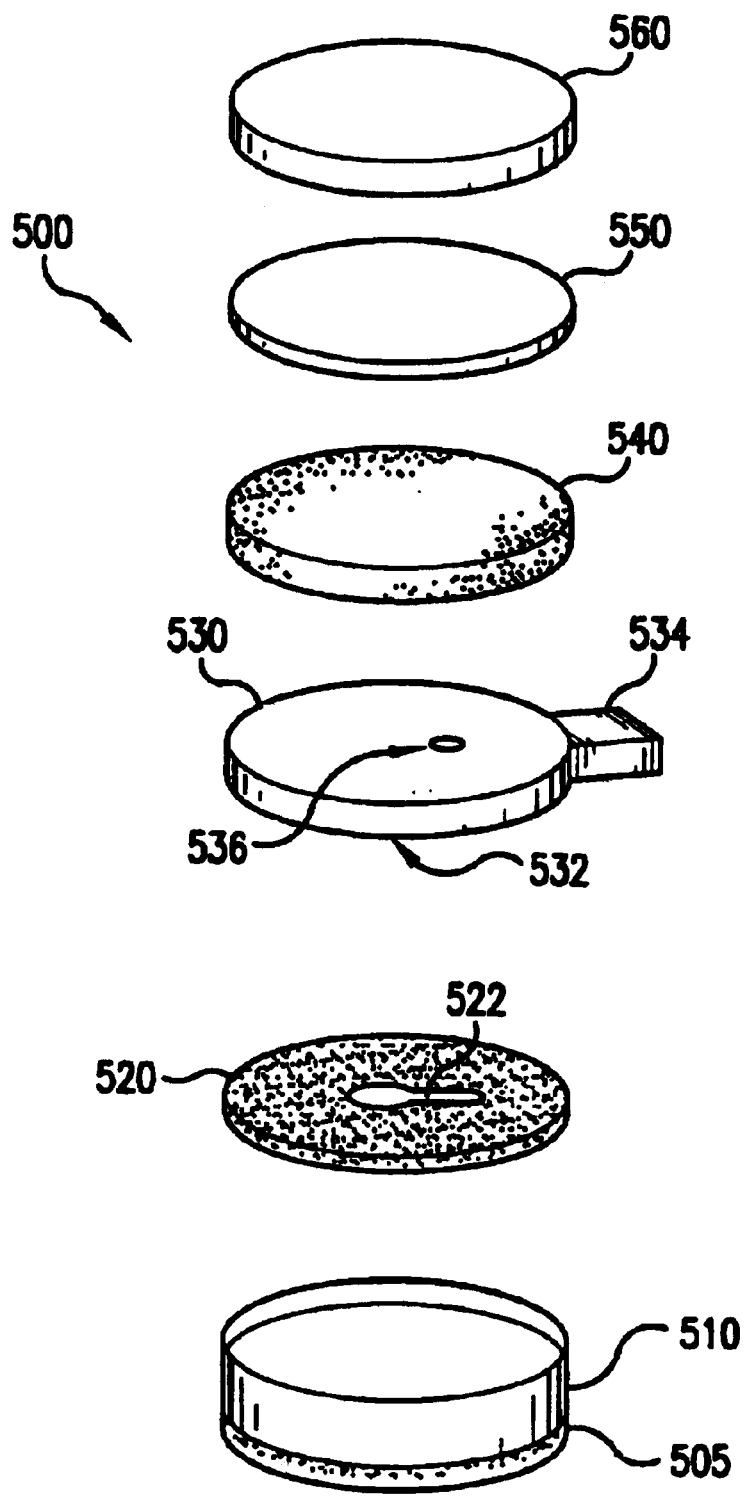
FIG. 4 is an exploded view of a fluid collection and sensor device featuring a waste fluid storage element according to another embodiment of the present invention.
Figure 5:
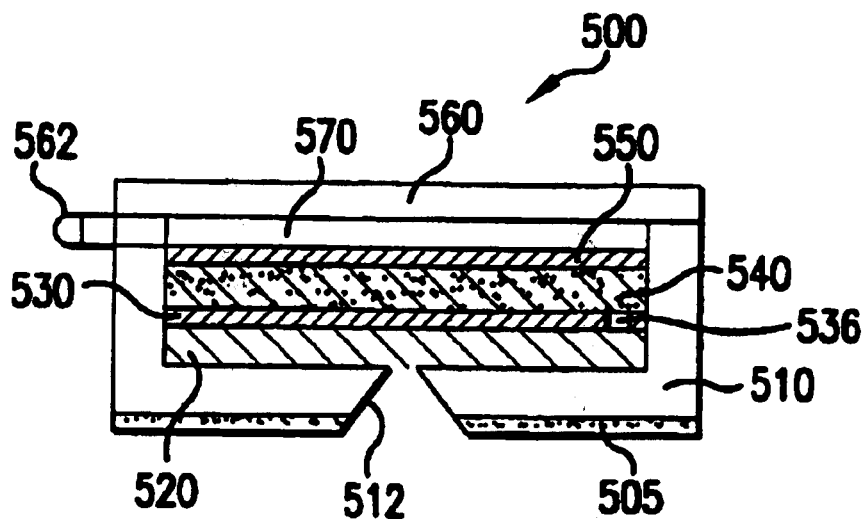
FIG. 5 is a cross-section view of the fluid collection and sensor device of FIG. 4, shown in assembled form.
Figure 6:
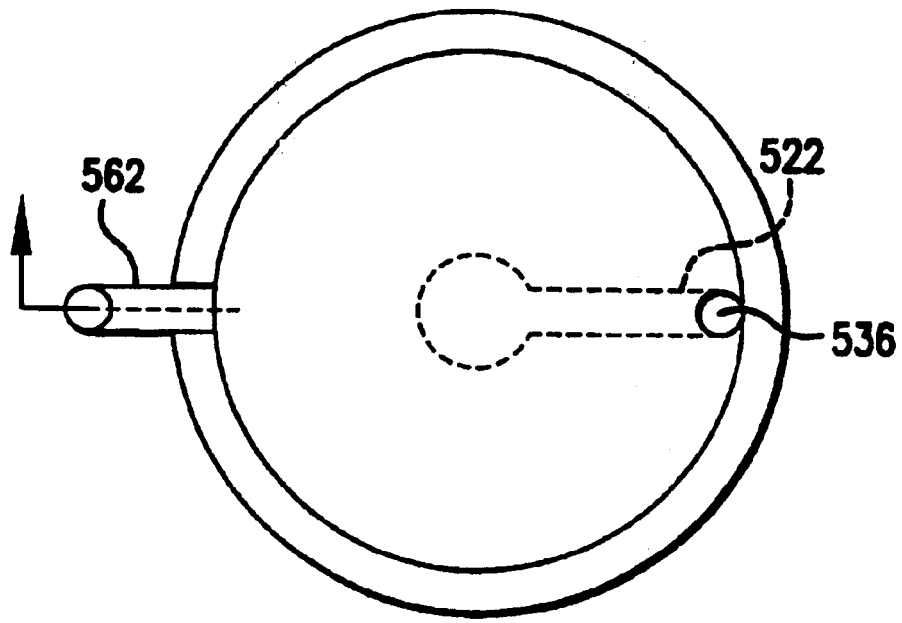
FIG. 6 is a top view of the fluid collection and sensor device of FIG. 4.

Referring to FIGS. 4–6, a fluid collection and sensor device featuring another configuration of a waste fluid storage element is shown. The fluid collection and sensor device 500 comprises a tissue interface member 510, a channel adhesive layer 520, an electrode substrate layer 530, an absorbent reservoir layer 540, an optional barrier layer 550 (which is optionally treated so as to be hydrophobic) and a top layer 560. The tissue interface member 510 is formed of a pliable material and has a contoured hole 512 which is aligned with one or more openings in the biological membrane when in use. A tissue adhesive layer 505 is optionally provided on the bottom of the tissue interface member 510 to attach to a surface of a biological membrane and form a pneumatic seal thereto, as well as to maintain continuous registration of the contoured hole 512 (referred to hereinafter) with the artificial openings formed in the organism.

The radius profile of this hole is important for maximizing the flux of fluid while minimizing local trauma to adjacent tissues. An effective range for the radius of this contoured hole is 0.1 mm to 10 mm. This contour may have a changing radius shape, such as that of an exponential curve or hyperbolic curve.

The channel adhesive layer 520 fits within the tissue interface member 520 and comprises a channel 522 that is laser or die cut therein. The channel adhesive layer 520 serves as a pneumatic seal around the channel 522 and to limit the volume of fluid exposed to the sensor (electrodes 532 referred to hereinafter). One end of the channel 522 in the channel adhesive layer is aligned with the hole 512 in the tissue interface member 510.

The electrode substrate layer 530 comprises several electrodes 532 (such as a working electrode, counter electrode and reference electrode) that are disposed on the bottom surface of the layer 530. For example, the electrode substrate layer 530 is formed of a polyester substrate material. Extending off of the electrode substrate layer 530 is an electrical connector 534 that contains leads which are electrically connected to the electrodes 532. A small hole 536 is provided in the electrode substrate layer 530 that communicates vacuum to the lower portions of the device 500 (in particular the channel 522 and the contoured hole 512) through which fluid is drawn upwards across the electrode substrate layer 530. The electrode substrate layer 530 is essential the sensor element of the fluid collection and sensor device 500. The electrodes 532 are formed on the electrode substrate layer 530 using screen printing, lithographic techniques, masked electro-deposition techniques, die or laser cut layers bonded to adjacent layers, or any combination of these methods or other suitable technologies known in the art.

A flow path for the biological fluid is defined in the device 500 by the hole 512 in the tissue interface member 510 and adhesive layer 505, channel 522 in the channel adhesive layer 520 and hole 536 in the electrode substrate layer 530 that leads to the absorbent reservoir layer 540.

The absorbent reservoir layer 540 is formed of the materials described above in conjunction with FIGS. 2 and 3. The optional barrier layer 550 may be formed of a suitable hydrophobic material, such as PTFE, Hyrdolon Nylon 6,6 (sold by Pall Specialty Materials, Port Washington, N.Y.) with a suitable pore diameter (0.2 μm to 0.22 μm) commonly used in membranes that filter fluid vapor from vacuum lines. The hydrophobic membrane layer 550 allows air to pass but blocks aerosols and aqueous liquids from passing through therethrough. The membrane material selected has pores of sufficiently small diameter to restrict movement of fluid, yet large enough to not create a pressure drop across the membrane. Such a pressure drop would have the result of decreasing the vacuum pressure at the sensor and reservoir level (512, 522, 536, and 540) of the fluid channel than that which would be detected by the pressure sensor near the vacuum pump (in 200).

Finally, the top layer 560 is formed of a suitable pliable material such as thin acrylic. A vacuum port 562 is provided on one end of the top layer 560 to communicate vacuum to the device 500. Optionally, a region of empty space 570 may be provided between the top layer 560 and the hydrophobic membrane layer 550 (if it is included) or between the top layer 560 and the absorbent reservoir layer 540 (if the barrier layer 550 is not included). The space 570 also serves to extend the useful lifetime of the hydrophobic membrane layer 550. Alternatively, the region of empty space may be positioned between the electrode substrate layer 530 and the absorbent reservoir layer 540.

The dimensions of the fluid collection and sensor device 500 vary depending on a particular application. As an example, the external dimensions of the tissue interface member 510 ranges in height from 1 mm to 10 mm and in diameter from 10 mm to 30 mm., with a total internal fluid volume capacity ranging from 10 μL to more than 2.0 mL. The electrode substrate layer 530 is for example 250 μm thick. The absorbent reservoir layer 540 is 2 mm thick. The optional barrier layer 550 (whether hydrophobic or not) 550 is 50 μm thick and the top layer 560 is 1 mm thick. For a particular reservoir material, there may be approximately 80–85% void volume or empty space available for fluid. For an absorbent material in a 25 mm diameter disc configuration with 80% void volume the thickness of the of the disc-shaped waste fluid reservoir element 540 required to hold 1 mL is approximately 2.5 mm. The reservoir layer is preferably capable of storing approximately 1 mL of fluid to accommodate a filling rate of 10 μL/hr over 72 hours.

In operation, the fluid collection and sensor device 500 is positioned on or about a biological membrane in which one or more artificial openings have been formed from which biological fluid will be harvested. Suction is applied at the port 562 to draw fluid into the device through the hole 512 and via the channel 522 in the adhesive layer 520 across the electrode substrate layer 530. As fluid is drawn across the electrode substrate layer 530, it is ultimately pulled through the hole 536 and into the absorbent reservoir layer 540. In addition, the capillary/wicking action of the absorbent reservoir layer 540 assists in pulling fluid into it. Fluid drawn across the electrode substrate layer 530 will be present for a sufficient amount of time in order to obtain an accurate reading of that sample of fluid, before it is drawn into the absorbent reservoir layer 540. The amount of suction applied to the device 500 and the wicking force of the absorbent reservoir layer 540 are controlled to ensure that the fluid stays on the electrode substrate layer 530 long enough to obtain an accurate reading. For example, it has been shown experimentally that a suction level of ¼ to ½ atmospheres and a Transorb™ wicking material achieves a sufficient dwell time on the sensor for accurate readings to be achieved. The optional hydrophobic membrane layer 550 prevents any of the biological fluid vapor from getting further downstream in the system and potentially contaminating the pump or pressure transducer. In addition, the hydrophobic membrane layer 550 provides a protective barrier to prevent contagious diseases from being spread between patients during successive uses of a monitor and control unit 200. The region 570 of empty space, if provided between the electrode substrate layer 530 and the absorbent reservoir layer 540, is useful to avoid clogging at the junction thereof. Fluid will fill the region of empty space prior to being drawn into the absorbent reservoir layer 540.

The material used in forming the absorbent reservoir may be treated with an anti-coagulant, anti-microbial or protease-active material to limit protein precipitation or build-up by other substances found in biological fluid (such as in blood or interstitial fluid) which may cause blockage at the entry point to the absorbent reservoir. Similarly, the channel in the adhesive layer may be treated with an anti-coagulant, anti-microbial or protease-active material material. Other substances may be used to treat various portions of the device to maintain fluid flow, including anti-microbials, collagenase, surfactants, hydrophilic substances, hydrophobic substances, or combinations thereof.

Figure 7:
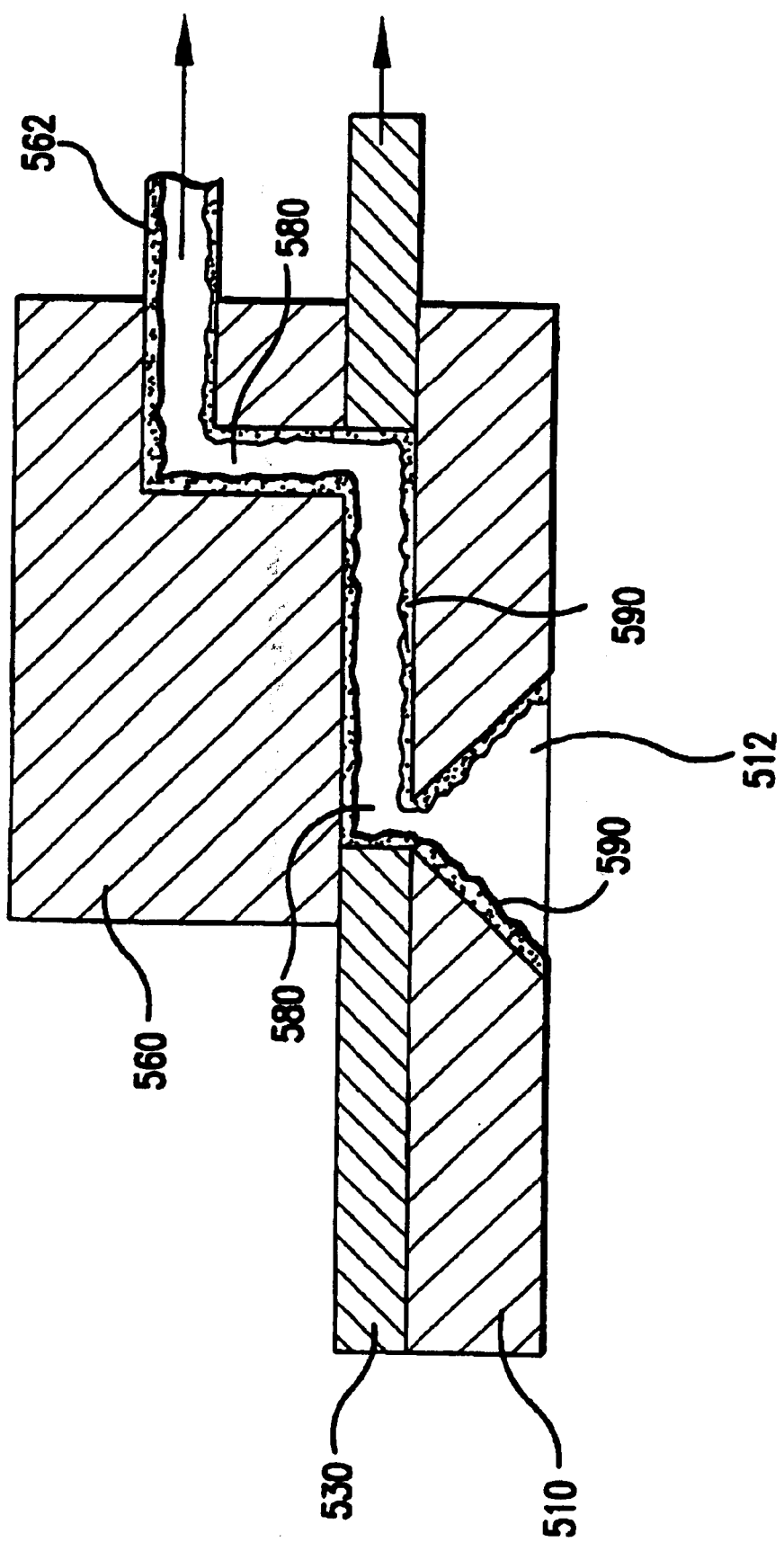
FIG. 7 is a cross-section view of a portion of a fluid collection and sensor device illustrating treatment of various components of the device with agents according to another aspect of the invention.

Another aspect of the invention is to treat various components of the fluid collection and sensor device with one or any combination of an anti-coagulant agent, anti-microbial agent or collagenase agent to prevent fibrin or protein build-up, sepsis and subsequent degradation or clogging of the flow path. With reference to FIG. 7, this aspect is described in greater detail. In this diagram, the reservoir layer and the adhesive layer are omitted to illustrate aspects of the invention that do not necessarily require the provision of these elements. In addition, since the adhesive layer is not included in this embodiment, the channel is cut in the electrode substrate layer 530 instead. The fluid path referred to above is shown particularly at reference numeral 580. In order to maintain the flow of biological fluid through the fluid collection and sensor device, surfaces of the fluid flow path 580 are treated with an anti-coagulant agent 590. The components of the device 500 that are treated include the surfaces of the opening 512 in the tissue interface member 510, the surfaces of the channel that is made in the electrode substrate layer 530, and the surfaces of the flow path that lead to the vacuum port 562. Alternatively, each of these components 510, 512, 530 and 562 are fabricated with a material embedded with some or all of these treatment compounds, in a manner similar to known controlled release implants or patch drug delivery systems.

An example of a suitable anti-coagulant agent is a heparin-based agent. One procedure to treat the surfaces with a heparin-based agent is as follows. Several mL of a Heparin-Benzalkonium Chloride (H-BAC) solution with a concentration of 720 units of heparin was loaded into a syringe with a luer connector. The syringe is connected to the vacuum port end of the tubing portion of the connector 300 (FIG. 1) and the H-BAC solution is introduced into the tubing until the entire tubing and the fluid flow path of the fluid collection and sensor device is filled up, making sure there are no bubbles present. Next, all of the H-BAC solution is retracted back into the syringe or push through the device into another container. Next, the device is connected to a high-pressure air source and air is run through the devices for 2–3 minutes to remove any solution remaining in the device. The device is then allowed to dry for several hours at ambient temperature, or the drying process can be expedited by drying it at a higher temperature for several minutes. Some other anti-coagulant agents include salicylic acid (aspirin), hyaluaronidase, various protease active agents such as collagenase, dilute solutions of ammonia, EDTA, apotinin, and a host of other compounds well known in the art and common in a standard clinical laboratory.

Further still, the components of the fluid flow path (in the embodiments with or without the reservoir and the adhesive layer), including the waste fluid storage element of the device are optionally treated with anti-bacterial agents to prevent an infection (bacteria) from growing in the fluid collection device and reaching further downstream in the system (even if a hydrophobic barrier layer is provided). Many anti-microbial products are also suitable, such as iodine, betadine, bacitracin, chlorophyll, EDTA, polysorbate-80, and apotinin, all of which could be incorporated as a surface treatment, or embedded in these components.

In addition, the components of the fluid flow path in the device (including the waste fluid storage element) can be treated by various surface modification techniques such as gas plasma, flame, chemical or corona discharge. Using one of these techniques, the surface can be modified with the optimal surface charge and charge density in order to prevent binding of the components of the biological fluid and to maintain sufficient wettability of the surfaces. Depending on the biological fluid that is being sampled, the treatment is applied such that the resultant net charge of the surface after modification is positive, negative or neutral.

Still further, the fluid collection and sensor device is optionally manufactured using micro-lithographic techniques as described in U.S. Provisional Application No. 60/092,731 filed Jul. 14, 1998, entitled "Integrated Device for Collecting a Micro-Fluid Sample and Assaying of Sample Utilizing Micro-Lithographic Bio-Sensor Component," the entirety of which is incorporated herein by reference. Micro-lithographic fabrication techniques are useful in constructing the sort of precision, micro-fluidic pathways and structures. An enhancement of the micro-fluid management could also be realized if the geometry of the tissue interface device were formed such that over the broad areas of the enzyme-laden portion of the sensor, a series of micro-channels or perforations are made that increases the ratio of surface area to internal volume of the porous sensor thereby facilitating a more rapid uniform wetting of the entire porous element and similarly rapid and complete "un-wetting" during the blotter removal phase to clear the old fluid away.

Figure 8:
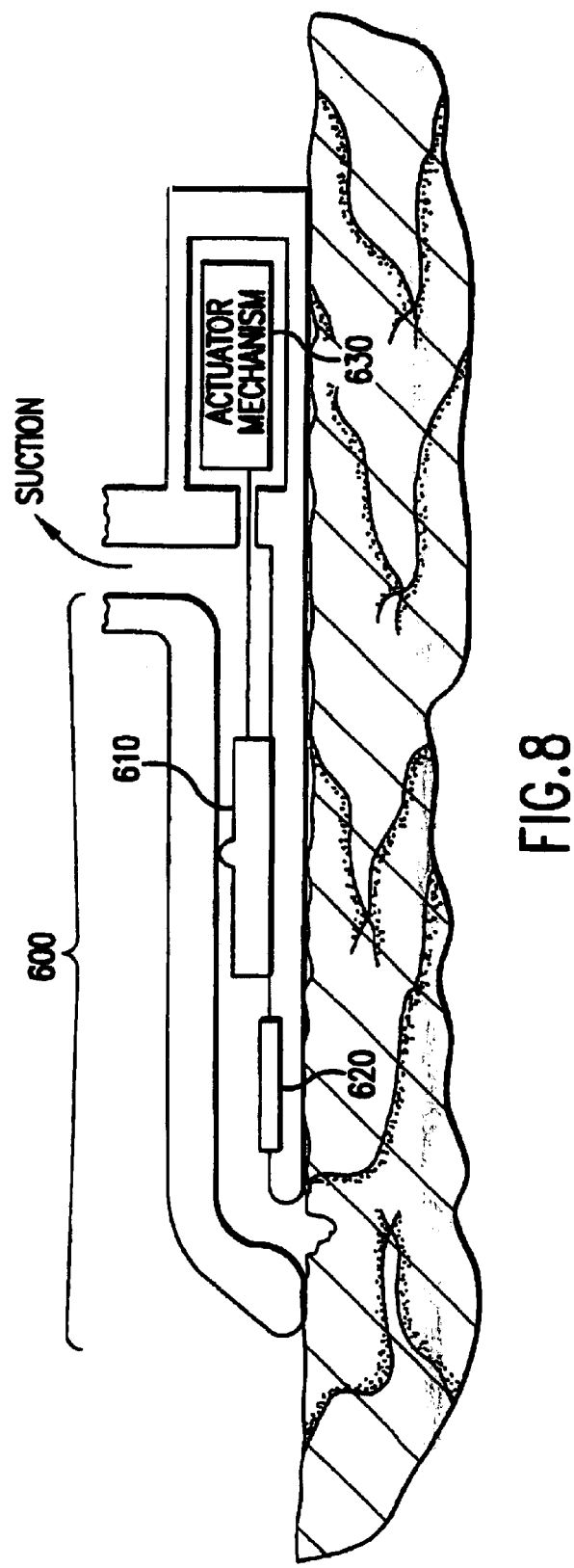
FIG. 8 is a partial cross-section view of a portion of a fluid collection and sensor device featuring a movable reservoir for removing fluid from the sensor according to another embodiment of the invention.

Referring to FIG. 8, another embodiment of a fluid collection and sensor device 600 is shown featuring a movable reservoir 610 in the form of a blotting element that is controllably positioned into and out of contact with the sensor 620 by an actuator mechanism 630. The actuator mechanism 630 is, for example, a miniaturized solenoid or other suitable mechanism capable of moving the blotting element into and out of contact with the sensor 610. This configuration achieves the delivery of fresh fluid in sufficient amounts to the sensor 610 on demand by momentarily moving the blotting element into contact with the sensor 620 to remove all previous fluid from the active regions and thereby ensure that the next assay reading would be made on a substantially new and current fluid sample. The material of the blotting element may be any one of the aforementioned absorbent materials useful for the reservoir described in the previous embodiments.

Figure 9:
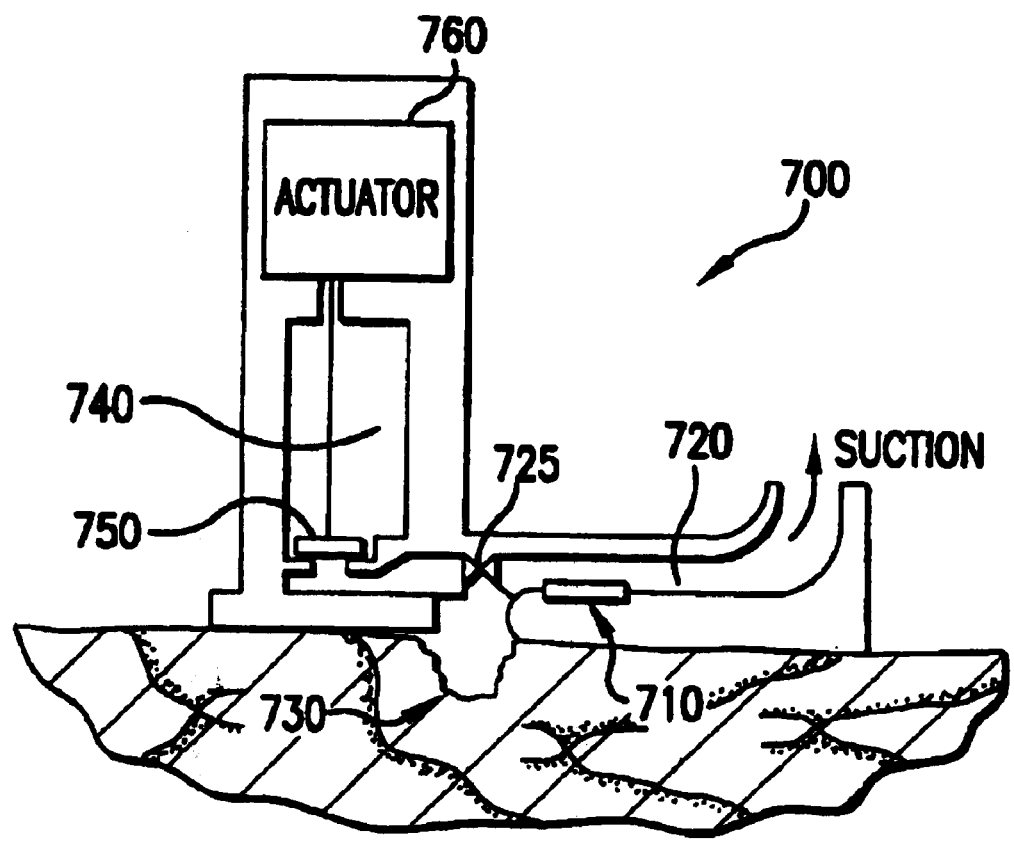
FIG. 9 is a partial cross-section view of a portion of a fluid collection and sensor device featuring an active suction and purge media arrangement according to yet another embodiment of the invention.

FIG. 9 illustrates an embodiment of a fluid collection and sensor device 700 featuring two other ways to remove "old" fluid from the sensor. One configuration comprises a fluid suction mechanism interfaced to the sensor such that when activated, old fluid is drawn off of the sensor. For example, the sensor 710 is placed within a small channel 720 defined by the tissue interface member, enclosed on all sides with both ends open. One end of the channel 720 is connected to a suction source (in the monitor and control unit 200) and the other end is connected to the fluid source 730, i.e., the fluid sample from the biological membrane. Under control of signals from the monitor and control unit 200, application of suction is applied to the channel 720 to flush the old fluid out of the sensor 710. A valve 725 is positioned over the entrance to the channel 720 to allow the suction to remove the old fluid. The valve 725 is controlled to open and thereby allows the suction force that is currently on in the channel 720 to flush the channel 720. The suction force could be increased as well. Once the valve 725 is closed, the fluid can again be pulled from the fluid source 730 and refill the channel 720. The dimensions of the channel 720 and the sensor 710 are made to contain a total volume of only a few microliters of fluid. Therefore, the fluid harvesting flux rates ensure that a volume of fluid is replaced completely every 30 seconds or less, thereby ensuring that readings taken periodically every 30 seconds will be largely independent of previous flow sample readings. This "flow purging" is optionally enhanced by adding a reservoir 740 of a purge media, such as water or an air bubble, that flushes the sensor 710 clean of the old fluid as the suction moved old fluid off of the sensor 710 prior to the introduction of the new fluid. A small valve 750 controlled by an actuator 760 opens or closes to control when the purging media is released across the sensor 710. The valve 750 is opened to release the purge media and is closed when a fresh fluid measurement is to be made, while keeping the suction on the channel 720 active through these cycles. The use of an air bubble effectively demarcates the segments of biological fluid in time and does not allow adjacent fluid segments to affect each other. The use of water is not optimal in terms of maintaining the separation of fluid segments and hence analyte concentration in time, but allows the addition of aqueous agents.

This active flow purging mechanism ensures that there is substantially complete fluid independence on the readings. Additionally, the purge media is optionally formulated to contain the anti-coagulants, anti-microbials, or other fluid management compounds that are useful in maintaining the integrity of the sensor and the overall functionality of the fluid collection and sensor device.

Micro-lithographic, direct laser machining, electroforming fabrication techniques or molds made from masters using these techniques are very useful in constructing the sort of precision, micro-fluidic pathways and structures. An enhancement of the micro-fluid management could also be realized if the geometry of the tissue interface device were formed such that over the broad areas of the enzyme laden portion of the sensor, a series of micro-channels or perforations are made that increases the ratio of surface area to internal volume of the porous sensor thereby facilitating a more rapid uniform wetting of the entire porous element and similarly rapid and complete "un-wetting" during the blotter removal phase to clear the old fluid away.

Figure 10:
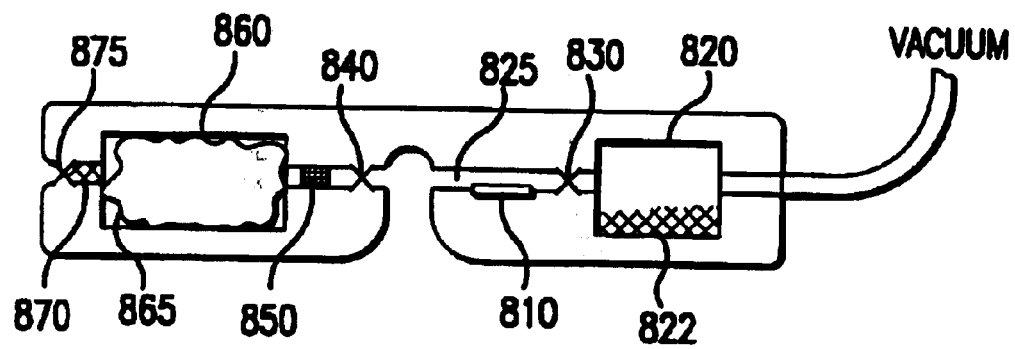
FIG. 10 is a partial cross-section view of a portion of a fluid collection and sensor device featuring one or more valves for controlling evaporation of fluid in the fluid flow path.

Turning to FIG. 10, still another feature of the invention is described. The device 800 shown in FIG. 10 features a sensor 810, a waste fluid storage element 820 (with an optional layer of absorbing material 822), a valve 830 between the sensor 810 and the waster fluid storage element 820, a valve 840, a filter 850, a reservoir 860 for containing a flushing fluid within an elastic bag 865, a gas permeable membrane 870 and a valve 875. Suction is applied from the monitor and control unit 200 either continuously (after the artificial openings are formed) or only prior to or during a sensor reading event. Since suction may not be constantly applied, the valve 830, placed in the fluid flow path 825 is closed, so that natural evaporation of excess fluid in the fluid flow path 825 occurs when the vacuum (or pressure) is not running. If the vacuum is shut off but not released, there still may be vacuum pressure in the fluid flow path 825 and thus natural evaporation could not occur, but rather vacuum pressure assisted evaporation could. The valve 830 is, for example, an impermeable flap. A sensor mounted externally on the device 800 is optional to detect when a shower, bath, rain or other ultra-high humidity condition is present to control activation of suction and appropriate valve control to maintain system integrity and functionality under these conditions.

The operation of the reservoir 860 and, valve 840 is similar to that described above in conjunction with FIG. 9. The gas permeable membrane 870 is optionally used in place of the valve 875 to allow air to flow into the reservoir 860 to displace the volume of the reservoir during flushing of the channel 825. The configuration of FIG. 10 is suitable for operation independent of the orientation of the device 800 on a tissue surface, such as the forearm of an individual, which is typically moving frequently, because the fluid contained in the elastic bag exerts continuous pressure on the fluid against the valve 840.

Figure 11:
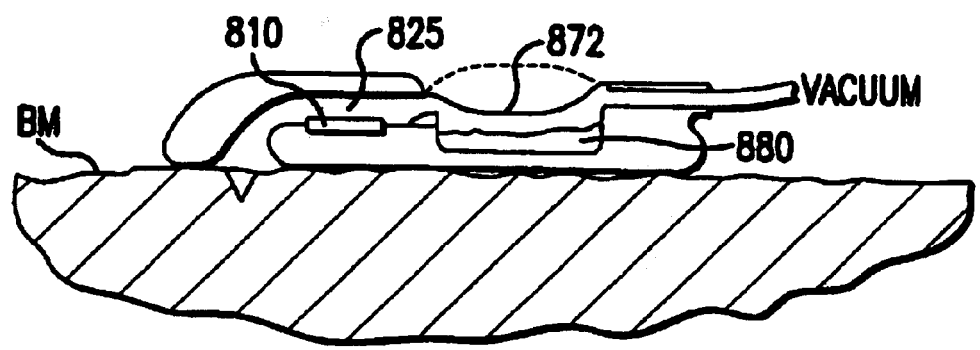
FIG. 11 is a diagram showing a fluid collection and sensor featuring a membrane or cover that controls evaporation of fluid in the device.

Turning to FIG. 11, the function of the valve 830 is also achieved with a reservoir 880 (that acts as the waste fluid storage element) having a membrane or cover 872 made of breathable material, such as GoreTex™ material. The cover 872 provides a vacuum tight seal when wetted with fluid, but still allows fluid to evaporate through the breathable membrane to remove fluid from the reservoir. The cover 872 is arranged to wet itself when vacuum is applied by bending down to touch the reservoir, but when vacuum is removed, the cover 872 would pull back up (as shown in phantom) and eventually dry to become permeable to water vapor, allowing the reservoir to dry out (but not to dry completely). In this scenario the reservoir 880 would be pre-wetted at manufacture. The membrane 872 is optionally treated with a protease active compound to prevent formation of skin over the membrane from protein and fibrin components in the biological fluid.

Figure 12:
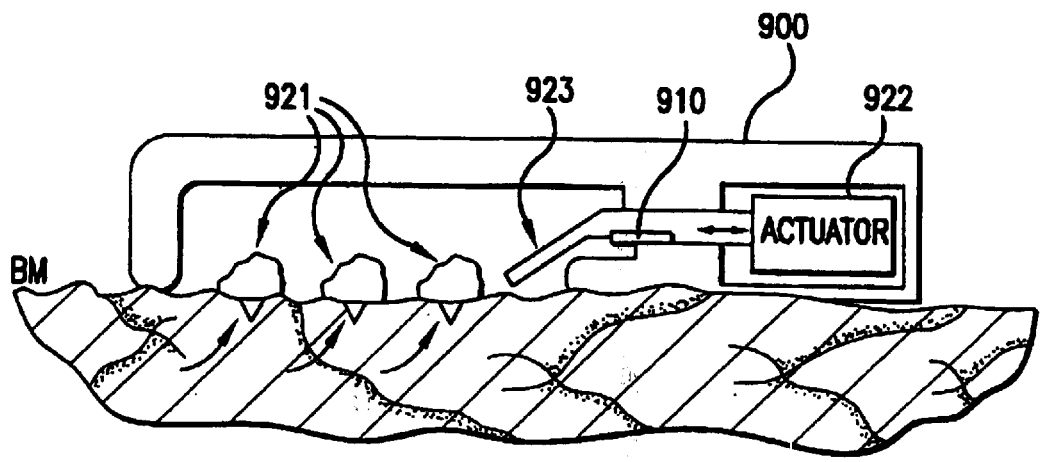
FIG. 12 is a diagram showing a fluid collection and sensor device featuring a capillary channel step-and-sip fluid control mechanism.

Turning to FIG. 12, another embodiment is shown wherein the fluid collection and sensor device 900 is optionally treated with a hydrophobic material that is transferred to the BM in order to cause the creation of fluid droplets 921 (as opposed to a continuous stream). The tissue interface device provides a physical reference to the artificial openings and fluid from each artificial opening. An actuator 922 and a capillary sipper 923 (e.g., a capillary tube) form a step-and-sip mechanism. The capillary tube has a first (input) end through which fluid is collected and a second end from which fluid is transported to the sensor 910. The actuator 922 moves the input end of the capillary sipper 923 sequentially to each fluid drop 921. Fluid moves through the capillary sipper 923 (as a result of the surface tension forces in the capillary tube) and out its second (output) end to make contact the sensor 910. Fluid is efficiently collected directly into the capillary tube 923 that feeds the sensor 910 with very little fluid waste to extraneous surface areas that exist in a passive fluid management configuration. This configuration is useful with or without the treatment of a hydrophobic compound.

Figure 13:
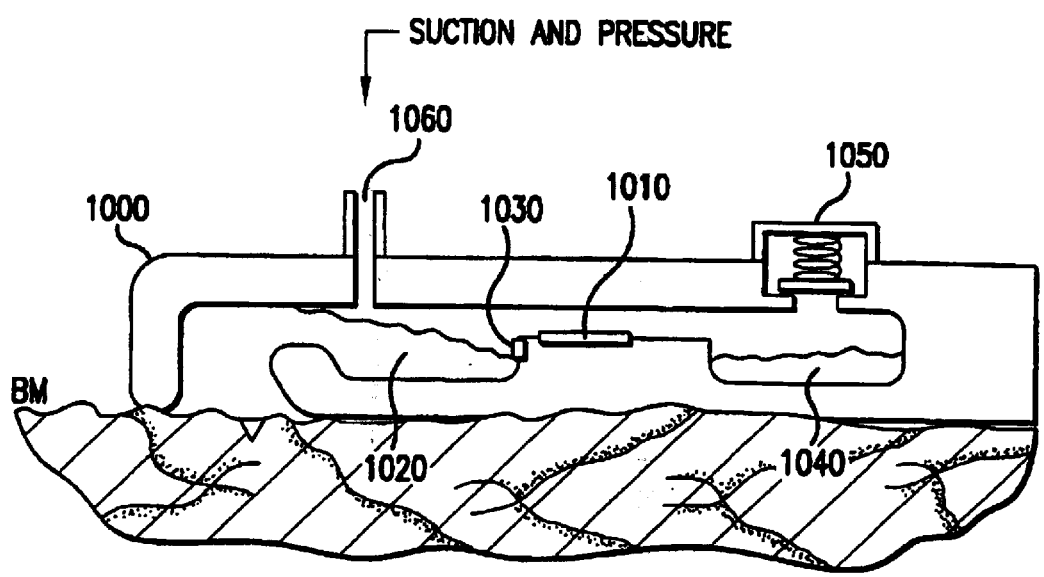
FIG. 13 is a diagram showing a fluid collection and sensor device featuring an intermediate reservoir useful in controlling fluid contact with the sensor.

Turning to FIG. 13, another embodiment is shown wherein the flow of sample fluid to the sensor is managed such that it is presented to the sensor in a fashion compatible with the proper performance of the sensor. The device, shown at reference numeral 1000, comprises a sensor 1010, a first or intermediate reservoir 1020, a volume sensor 1030, a waste reservoir 1040, and a check valve 1050. Suction is applied to the device 1000 via a suction port 1060. The intermediate reservoir 1020 accumulates the harvested fluid sample during the harvesting process until a sufficient volume of the fluid sample is obtained. The volume sensor 1030 detects when a sufficient volume of fluid has been collected in the intermediate reservoir 1020. The volume sensor 1030 is, for example, an electrical sensor, optical sensor, sonic sensor or the like and sends a signal to the monitor and control unit 200 alerting it that the tissue interface device can deliver the sample to the sensor 1010. In operation, suction is applied initially to draw fluid into the intermediate reservoir 1020. When the volume sensor 1030 triggers, the monitor and control unit 200 replaces the suction with a mild pressure for a controlled time period, causing the check valve 1050 to open and force fluid onto the sensor 1010. The fluid is allowed to dwell on the sensor 1010 for a sufficient period of time to obtain a reading. After the measurement is complete, the monitor and control unit applies an additional small amount of pressure to force the fluid from the sensor 1010 to the waste reservoir 1040. When a fresh fluid sample is desired, the application of suction closes the check valve and induces fresh fluid to enter the intermediate reservoir 1020, and the process repeats.

Turning to FIGS. 14–16, another embodiment is shown featuring electrodes of an electrochemical bio-sensor which are disposed on the inside walls of a micro-capillary tube. The device 1100 comprises a housing 1101, a tissue interface element or member 1105 having a contoured interface hole 1115, a capillary tube 1120 and a sensor 1125 disposed on an interior wall of the capillary tube 1120. A sensor interconnect fitting 1130 is mounted on the outside wall of the capillary tube 1120 and feeds the electrical lead lines 1135 to a hole in the fluid collection device housing 1101. An optional translation stage 1140 provides translation which may be required to gain access to all of the fluid bead, depending on the size of the capillary tube 1120 used and the number of artificial openings 1110 made in the organism. Electrical leads 1130 connect to the sensor 1125, which are in turn, connected to the monitor and control unit 200. A fluid wicking and evaporation element 1150 (such as a fiber plug) is provided at one end of the capillary tube. As shown in FIG. 16, the sensor 1125 includes sensor electrode wires 1126 that are disposed on inside walls of the capillary tube 1120 using any known technique suitable therefor. The electrode wires 1126 comprise a working electrode (W), a counter electrode (C) and a reference electrode (R).

The device 1100 is aligned with one or more artificial openings 1110. The biological fluid is drawn out of the artificial opening(s) 910 in the organism through the contoured hole 1115 in the tissue interface element 1105 and forms a bead of fluid 1112 at the surface of the biological membrane of the organism. As the bead of fluid 1112 grows and comes in contact with the entry point of the capillary tube 1120, biological fluid is drawn into the capillary tube 1120 by capillary action. The capillary tube 1120 may be coated by various agents to enhance the capillary action of the tube. As the fluid moves up the capillary tube 1120, it comes into contact with the sensor 1125 which is mounted on the inside wall of the capillary tube 1120. The fluid collection device 1100 is under vacuum pressure from the monitor and control unit 200 through the vacuum port 1160. In addition, the vacuum chamber formed by the device housing 1101 and the tissue interface element 1105 is optionally pre-humidified to reduce errors due to the evaporation of the biological fluid as it comes out of the artificial openings in the organism. In another embodiment, optical detection of the analyte of interest is utilized. An optical fiber is substituted for the electrode wires 1126 in the sensor 1125 and for the electrical wires 1135 for use with an optically read sensor. The rate of sample change is as rapid as new fluid sample is made available. In this manner, evaporation of the sample under measurement is minimized.

The capillary tube is constructed in such a manner that its thickness (optical path) can be varied in a manner similar to the dimensional changes used in pulse oximetry. From the introduction of a simulated photoplethysmographic waveform, the optical absorption is measured at various wavelengths and at multiple absorption path lengths allowing a ratio-metric calculation to measure the levels of a specific analyte desired.

In all of the foregoing embodiments, before the fluid collection and sensor device 100 is applied to the BM, the site on the BM where the artificial openings are to be formed may be treated with a ring-shaped area of a hydrophobic material, except for an area defining a capillary or wicking channel that abuts the site. This treatment facilitates delivery of the biological fluid into the device.

The above description is intended by way of example only and is not intended to limit the present invention in any way except as set forth in the following claims.

What is claimed is:

1. A fluid collection and sensor device for placement over at least one artificial opening made in a biological membrane for measuring a characteristic of a biological fluid collected from the tissue through the at least one artificial opening, the device comprising:
    a sensor positioned in a flow path of the biological fluid for contacting a quantity of the biological fluid and generating an indication of a characteristic of the biological fluid;
    a reservoir positioned in the device to collect the biological fluid after it has made contact with the sensor; and
    a barrier layer positioned between the reservoir and a source of vacuum that is applied to the device for drawing biological fluid across the sensor from the tissue.

2. The device of claim 1, wherein the reservoir comprises an absorbent material.

3. The device of claim 2, wherein the reservoir comprises one or more layers of bonded fibers.

4. The device of claim 1, wherein at least the flow path and/or reservoir is treated with an agent to limit or minimize clotting, aggregation or sepsis of the biological fluid, blockage or clogging of the flow path or degradation of the sensor.

5. The device of claim 4, wherein the agent is an anticoagulant.

6. The device of claim 4, wherein the agent is an antimicrobial.

7. The device of claim 4, wherein the agent is a surfactant.

8. The device of claim 1, wherein the barrier layer is positioned offset from the source of vacuum pressure so that there is an open space between it and the source of vacuum.

9. The device of claim 1, wherein the reservoir is positioned offset from the sensor so that there is an open space between it and the sensor.

10. The device of claim 1, wherein the barrier layer is formed of hydrophobic material or a material treated with a hydrophobic substance.

11. The device of claim 1, wherein the barrier layer comprises a porous material having a pore diameter sufficient to prevent vapor from the biological fluid from escaping from the device.

12. The device of claim 1, wherein the volume capacity of the reservoir is 0.1 mL to 2 mL.

13. The device of claim 1, and further comprising a tissue interface member having at least one aperture therein to be positioned in alignment with the at least one artificial opening in the tissue.

14. The device of claim 1, wherein the reservoir is movable into contact with the sensor to remove fluid therefrom, and further comprising an actuator mechanism coupled to the reservoir to move it into and out of contact with the sensor.

15. The device of claim 14, wherein the reservoir is a blotting element formed of an absorbent material.

16. The device of claim 1, and further comprising a membrane positioned over the reservoir, wherein the membrane is responsive to suction applied to the device to make contact with fluid in the reservoir and seal the reservoir, and is responsive to the removal of suction to bend away from the reservoir and allow fluid from the reservoir to evaporate.

17. The device of claim 1, and further comprising:
   an intermediate reservoir positioned in the device to accumulate fluid prior to delivery to the sensor;
   a volume sensor positioned proximate the intermediate reservoir to sense when sufficient volume of fluid has accumulated in the intermediate reservoir;
   a valve that is caused to open when the volume sensor has detected that a sufficient volume of fluid has accumulated in the intermediate reservoir thereby forcing fluid from the intermediate reservoir onto the sensor.

18. The device of claim 17, wherein fluid is moved from the sensor to the waste fluid reservoir in response to application of pressure.

19. The device of claim 17, wherein the valve is responsive to suction applied to the device to close and induce fresh fluid to enter and accumulate in the intermediate reservoir.

20. A fluid collection and sensor device for placement over at least one artificial opening made in a biological membrane for measuring a characteristic of a biological fluid collected from the tissue through the at least one artificial opening, the device comprising:
   a tissue interface member comprising at least one aperture for being positioned in alignment with the at least one artificial opening in the biological membrane;
   a sensor positioned for measuring a characteristic of the biological fluid that is collected by the device;
   a reservoir positioned proximate the sensor that collects biological fluid after it makes contact with the sensor;
   a port suitable for connection to a suction source; and
   a barrier layer positioned adjacent the reservoir and the port.

21. The device of claim 20, wherein the barrier layer is formed of hydrophobic material or a material treated with a hydrophobic substance.

22. The device of claim 20, wherein the barrier layer comprises a porous material having a pore diameter sufficient to prevent vapor from the biological fluid from escaping from the device.

23. The device of claim 20, wherein the reservoir is positioned offset from the sensor such that there is empty space in the device between it and the sensor.

24. The device of claim 20, wherein the sensor comprises a layer of material that is sensitive to an analyte.

25. The device of claim 20, wherein the sensor comprises a substrate layer and defining a hole for receiving fluid into the substrate layer.

26. The device of claim 25, and further comprising a layer positioned adjacent the substrate layer and comprising a channel therein to transport fluid to the hole of the substrate layer.

27. The device of claim 20, wherein the reservoir comprises an absorbent material.

28. The device of claim 27, wherein the reservoir comprises one or more layers of bonded fibers.

29. The device of claim 27, wherein the absorbent material is treated with an anti-coagulant agent.

30. The device of claim 20, wherein the reservoir is treated with an agent to limit or minimize clotting, aggregation or sepsis of the biological fluid, blockage or clogging of the flow path or degradation of the sensor.

31. The device of claim 30, wherein the agent is an anti-coagulant, anti-microbial or surfactant.

32. A fluid collection and sensor device for placement over at least one artificial opening made in a biological membrane for measuring a characteristic of a biological fluid collected from the tissue through the at least one artificial opening, the device comprising:
   a tissue interface member having an opening to receive biological fluid therethrough and defining a fluid channel;
   a sensor positioned in the fluid channel to measure a characteristic of the biological fluid that is collected by the device;
   a suction source coupled to an end of the fluid channel;
   a controller coupled to the suction source to control the application of suction to the fluid channel to draw fluid previously on the sensor off of the sensor and draw new biological fluid from the biological membrane onto the sensor;
   a reservoir containing a volume of purge media;
   a valve coupled between the reservoir and the fluid channel to control the delivery of purge media to the sensor;
   wherein the controller is coupled to the valve to open the valve for a period of time to release the purge media to clean off fluid from the sensor and to close the valve for a period of time during which new fluid is allowed to make contact with the sensor.

33. The device of claim 32, wherein the controller maintains application of suction to the fluid channel when the valve is open and when the valve is closed.

34. A fluid collection and sensor device for placement over at least one artificial opening made in a biological membrane for measuring a characteristic of a biological fluid collected from the tissue through the at least one artificial opening, the device comprising:
   a sensor positioned in a flow path of the biological fluid for contacting a quantity of the biological fluid and generating an indication of a characteristic of the biological fluid;
   a reservoir positioned in the device to collect the biological fluid after it has made contact with the sensor, wherein the reservoir is movable into contact with the sensor to remove fluid therefrom; and
   an actuator mechanism coupled to the reservoir to move it into and out of contact with the sensor.

35. A fluid collection and sensor device for placement over at least one artificial opening made in a biological membrane for measuring a characteristic of a biological fluid collected from the tissue through the at least one artificial opening, the device comprising:
- a sensor positioned in a flow path of the biological fluid for contacting a quantity of the biological fluid and generating an indication of a characteristic of the biological fluid;
- a reservoir positioned in the device to collect the biological fluid after it has made contact with the sensor; and
- a membrane positioned over the reservoir, wherein the membrane is responsive to suction applied to the device to make contact with fluid in the reservoir and seal the reservoir, and is responsive to the removal of suction to bend away from the reservoir and allow fluid from the reservoir to evaporate.

36. A fluid collection and sensor device for placement over at least one artificial opening made in a biological membrane for measuring a characteristic of a biological fluid collected from the tissue through the at least one artificial opening, the device comprising:
- a sensor positioned in a flow path of the biological fluid for contacting a quantity of the biological fluid and generating an indication of a characteristic of the biological fluid;
- a reservoir positioned in the device to collect the biological fluid after it has made contact with the sensor;
- an intermediate reservoir positioned in the device to accumulate fluid prior to delivery to the sensor;
- a volume sensor positioned proximate the intermediate reservoir to sense when sufficient volume of fluid has accumulated in the intermediate reservoir; and
- a valve that is caused to open when the volume sensor has detected that a sufficient volume of fluid has accumulated in the intermediate reservoir thereby forcing fluid from the intermediate reservoir onto the sensor.

37. The device of claim 36, wherein fluid is moved from the sensor to the waste fluid reservoir in response to application of pressure.

38. The device of claim 36, wherein the valve is responsive to suction applied to the device to close and induce fresh fluid to enter and accumulate in the intermediate reservoir.

39. A fluid collection and sensor device for placement over at least one artificial opening made in a biological membrane for measuring a characteristic of a biological fluid collected from the tissue through the at least one artificial opening, the device comprising:
- a tissue interface member comprising at least one aperture for being positioned in alignment with the at least one artificial opening in the biological membrane;
- a sensor positioned for measuring a characteristic of the biological fluid that is collected by the device;
- a fluid flow path extending from the opening in the tissue interface member across the sensor;
- a reservoir positioned proximate the sensor that collects biological fluid after it makes contact with the sensor;
- a port suitable for connection to a suction source; and
- a barrier layer positioned adjacent the reservoir and the port;
- wherein at least a portion of the surfaces of the aperture in the tissue interface member and of the fluid flow path is coated with an agent to limit or minimize clotting, aggregation or sepsis of the biological fluid, blockage or clogging of the flow path or degradation of the sensor.

40. The device of claim 39, wherein the agent is an anti-coagulant, anti-microbial or surfactant.

41. The device of claim 39, wherein the reservoir comprises an absorbent material.

42. The device of claim 41, wherein the absorbent material is treated with an anti-coagulant agent.

43. The device of claim 39, wherein at least a portion of the surface of the fluid flow path is treated so as to be positively charged.

44. The device of claim 39, wherein at least a portion of the surface of the aperture of the tissue interface member is treated so as to be positively charged.

* * * * *

UNITED STATES PATENT AND TRADEMARK OFFICE
CERTIFICATE OF CORRECTION

| | |
|---|---|
| PATENT NO. | : 7,037,277 B1 |
| APPLICATION NO. | : 09/357452 |
| DATED | : May 2, 2006 |
| INVENTOR(S) | : Alan Smith et al. |

It is certified that error appears in the above-identified patent and that said Letters Patent is hereby corrected as shown below:

On the Title page, in the field (75) labeled Inventors: please add to the bottom of the list the following --Mark Samuels, Norcross, GA (US)--.

Signed and Sealed this

Nineteenth Day of December, 2006

JON W. DUDAS
*Director of the United States Patent and Trademark Office*